United States Patent [19]

Wang et al.

[11] Patent Number: 5,847,212

[45] Date of Patent: Dec. 8, 1998

[54] PROCESS FOR THE PREPARATION OF IOHEXOL

[75] Inventors: Xiu Chun Wang, Gurnee; Ashok V. Bhatia, Libertyville; Steven A. Chamberlin, Waukegan, all of Ill.

[73] Assignee: Abbott Laboratories, Abbott Park, Ill.

[21] Appl. No.: 844,587

[22] Filed: Apr. 21, 1997

[51] Int. Cl.$^6$ .................................................. C07C 233/05
[52] U.S. Cl. .................................. 564/153; 424/9.452
[58] Field of Search ........................ 564/153; 424/9.452

[56] References Cited

U.S. PATENT DOCUMENTS

| | | | |
|---|---|---|---|
| 4,250,113 | 2/1981 | Nordal et al. | 564/153 |
| 4,348,377 | 9/1982 | Felder et al. | 424/5 |
| 5,191,119 | 3/1993 | Sovak et al. | 564/153 |
| 5,527,926 | 6/1996 | Ranganathan et al. | 549/480 |

FOREIGN PATENT DOCUMENTS

| | | |
|---|---|---|
| 532390 | 10/1984 | Spain . |
| 641191 | 12/1985 | Spain . |

OTHER PUBLICATIONS

J. Haavaldsen et al., "X-Ray Contrast Agents" ACTA Pharm. Suec. 20, 219–232 (1983).

*Primary Examiner*—Shailendra Kumar
*Attorney, Agent, or Firm*—Gregory W. Steele

[57] ABSTRACT

Provided is a novel process for the preparation of iohexol having reduced number of isolated intermediates and significantly reduces or eliminates the use of ion-exchange resins required to desalinate the final product.

16 Claims, No Drawings

PROCESS FOR THE PREPARATION OF IOHEXOL

TECHNICAL FIELD OF THE INVENTION

This invention relates to a process for the preparation of iohexol.

BACKGROUND OF THE INVENTION

There exist a number of prior art methods for the production of iohexol (5-[Acetyl(2,3-dihydroxypropyl)amino]-N,N'-bis(2,3-dihydroxypropyl)-2,4,6-triiodo-1,3-benzenedicarboxamide; CAS-66108-95-0), see, for example, U.S. Pat. Nos. 4,250,113 and 5,191,119, Spanish patents ES 532 390 and ES 541 191, and Haavaldsen, et al, Acta Pharm. Suec. 20: 219–232 (1983). However, prior art procedures are not always amenable to large scale production as they may require inconvenient separation steps or the use of difficult to handle reagents and/or result in relatively low yields. For instance, Haavaldsen, et al utilize a multistep procedure which isolates an intermediate by filtration from acetic anhydride/sulfuric acid. In addition, the yield from the first step is reported to be only 65%.

Another problem of existing methods is that in the final reaction step, the conversion of 5-acetamino-N,N'-bis-(2,3-dihydroxypropyl)-2,4,6-triiodo-1,3-benzenedicarboxamide to iohexol, can result in large quantities of sodium chloride as a byproduct. The removal of this salt thus requires ion-exchange resins resulting in increased cost and loss of product.

Thus there continues to be a need for an efficient method of producing iohexol with improved product purity.

BRIEF SUMMARY OF THE INVENTION

The present invention provides a process for making iohexol comprising the steps of combining 5-acetamino-N,N'-bis-(2,3-dihydroxy-propyl)-2,4,6-triiodo-1,3-benzene-dicarboxamide, a solvent, glycidol, and a base to form a reaction mixture, maintaining the reaction mixture for a period of time sufficient to allow the reaction to proceed to completion and isolating the iohexol.

DETAILED DESCRIPTION OF THE INVENTION

The following terms and abbreviations are used throughout this specification and appended claims.

"DBU" means 1,8-diazabicyclo[5.4.0]undec-7-ene.

"DBN" means 1,5-diazabicyclo[4.3.0]non-5-ene.

"DMSO" means dimethylsulfoxide.

"IPA" means isopropyl alcohol.

All chemicals used are of reagent grade or better and are commercially available (e.g., Sigma Chemical Company, St. Louis, Mo., Aldrich Chemical Company, Milwaukee, Wis.)

The present invention relates to a process of producing iohexol from 5-acetamino-N,N'-bis-(2,3-dihydroxypropyl)-2,4,6-triiodo-1,3-benzenedicarboxamide. The starting material can be obtained in any number of ways, se, e.g., the processes described in U.S. Pat. No. 4,250,113, Spanish Patents ES 541191 and ES 532390 or copending U.S. Patent application Ser. No. 08/721,431 filed Sep. 27, 1996. In accordance with the process of the invention, as described briefly here and in more detail below, Compound 1, 5-acetamino-N,N'-bis-(2,3-dihydroxypropyl)-2,4,6-triiodo-1,3-benzenedicarboxamide is converted to iohexol in a single step synthesis. The present invention provides a novel process for synthesizing the 2,3-dihydroxypropyl side chain of iohexol and improves upon the prior art methods by eliminating the use of chloride containing reagents and thus significantly reducing or eliminating the need for ion exchange resins to remove the resulting ions from the crude iohexol.

In accordance with the process of the invention, 5-acetamino-N,N'-bis-(2,3-dihydroxypropyl)-2,4,6-triiodo-1,3-benzene-dicarboxamide (Compound 1), solvent, glycidol and a catalytic amount, typically in the range of about 0.1 mole %, of a base, are combined to form a reaction mixture that is maintained for a period of time sufficient for the synthesis of iohexol to occur. Typically, the reaction mixture is maintained at 20° to 100° C. for 1.5 to 120 hours, more preferably at about 20° to 40° C. for about 36 to 96 hours.

A wide variety of solvents and bases are suitable for use in the process of the invention. Suitable solvents for the reaction mixture include DMSO, 2-methoxyethanol, or water. Suitable bases include carbonates, DBU, DBN, $C_1$–$C_4$ tertiary amines, N-methyl-morpholine, potassium, sodium and lithium alkoxides, and sodium, lithium and potassium hydroxides. As will be apparent to one skilled in the art, the selection of a base depends on its solubility with the remaining components of the reaction mixture. Thus, DMSO is preferred when the base is a tertiary amine, DBN, DBU, or hydroxide; water is preferred with a carbonate or hydroxides; and 2-methoxyethanol is preferred with hydroxides or alkoxides. Finally, crude iohexol is isolated in a suitable solvent, typically IPA and/or IPA in methanol, and the solids collected under nitrogen and washed with IPA. In those cases where the selection of solvents and bases leads to the production of sodium salts, desalination may be performed prior to recrystallization from methanol/IPA. In a preferred embodiment, desalination of the iohexol solution is avoided entirely by the use of a tertiary amine.

Importantly, the process of the invention avoids the use of epichlorohydrin or 3-chloro-1,2-propane-diol as taught in the prior art. Thus, the present invention does not require the removal of the sodium chloride as a byproduct of the synthesis.

The resulting iohexol can be collected and further purified using techniques well known in the art, for instance by recrystallization from butanol as described in U.S. Pat. No. 4,250,113, which is incorporated by reference.

The following Examples illustrate embodiments of the invention and are not intended to limit the specification and claims in any way.

EXAMPLE 1

40 g of Compound 1 was treated with 0.75 ml of triethylamine and 60 ml of DMSO at 100° C. for 5 minutes to dissolve. The solution was cooled to room temperature under nitrogen. Glycidol (6.0 g) was added and the solution was mixed at 40° C. for four days. HPLC showed 92% iohexol. The solution was cooled to room temperature and added to 500 ml of Isopropanol. The solids were filtered under nitrogen and dried under vacuum to give 40 g of iohexol.

EXAMPLE 2

20 g of Compound 1 was treated with 0.15 g of potassium hydroxide and 30 ml of DMSO at 90° C. for 5 minutes to dissolve the solids. The solution was cooled to room temperature under nitrogen. Glycidol (3.0 g) was added and the solution was mixed at room temperature for four days.

The solution was added to 300 ml of isopropanol. The solids were filtered under nitrogen and then dissolved in 200 ml of methanol. The solution was evaporated under nitrogen to give 18 g of iohexol. The solids were dissolved in 80 ml of distilled water and treated with an ion exchange resin (Amberlyst-15 (H$^+$)) to remove residual potassium hydroxide. The resins were filtered and the solution was evaporated to dryness. 18 g of iohexol was obtained with 92% peak area by HPLC.

EXAMPLE 3

1 g of Compound 1 was treated with 1.5 ml of DMSO at 100° C. for 2 minutes to dissolve the solids. The solution was cooled to room temperature under nitrogen. DBU (20 mg) and glycidol (0.15 g) were added and the solution was mixed at room temperature for three days. HPLC showed 92% iohexol. The solution was added to isopropanol. The solids were filtered under nitrogen and dried under vacuum to give 40 g of iohexol.

EXAMPLE 4

1 g of Compound 1 was treated with 2 ml of DMSO at 90° C. for 5 minutes to dissolve the solids. The solution was cooled to room temperature under nitrogen. N-methylmorpholine (0.015 ml) and glycidol (0.15 g) were added. The solution was mixed at 40° C. for 40 hours. HPLC showed 90% iohexol. The solution was cooled to room temperature and added to 20 ml of isopropanol. The solids were filtered under nitrogen and dried under vacuum to give 0.8 g of iohexol.

EXAMPLE 5

5.0 gram 5-acetamino-N,N'-bis-(2,3-dihydroxypropyl)-2,4,6-triiodo-1,3-benzene-dicarboxamide (Compound 1), 0.36 gram of 25% sodium methoxide in methanol, and 1.5 gram glycidol are combined in 2-methoxyethanol and heated to 90° C. for four hours. Solvent is removed under vacuum followed by dissolution of the residue in water. The solution is treated with 1 gram each of Amberlyst A-15 and Amberlite IRA-67 ion-exchange resins to remove sodium methoxide. Water is removed under vacuum to afford an oil. Crystallization from methanol/isopropanol (10:75) afforded 3.5 gram (64.6%) iohexol.

EXAMPLE 6

Glycidol (0.25 gram) and 15% sodium hydroxide (0.11 gram) are added to a slurry of 2 gram Compound 1 in 13 gram water. After mixing at 50° C. for 18 hours, HPLC of the crude reaction mixture shows 81% iohexol. The product is crystallized as described above.

EXAMPLE 7

Glycidol (0.25 gram) and 15% sodium hydroxide (0.12 gram) are added to a slurry of 2 gram Compound 1 in 13 gram water. After mixing at 80° C. for 1.5 hours, HPLC of the crude reaction mixture shows 77% iohexol. The product is crystallized as described above.

EXAMPLE 8

Glycidol (0.25 gram) and sodium carbonate (0.04 gram) are added to a slurry of 2 gram Compound 1 in 13 gram water. After mixing at 50° C. for 72 hours, HPLC of the crude reaction mixture shows greater than 90% iohexol. The product is crystallized as described above.

We claim:

1. A process for making iohexol comprising the steps of:
   a. combining 5-acetamino-N,N'-bis-(2,3-dihydroxy-propyl)-2,4,6-triiodo-1,3-benzene-dicarboxamide, a solvent, glycidol, and a base to form a reaction mixture;
   b. maintaining the reaction mixture for a period of time sufficient to allow the reaction to proceed to completion; and
   c. isolating iohexol.

2. The process of claim 1 wherein the solvent is selected from DMSO, 2-methoxyethanol, or water.

3. The process of claim 1 wherein the base is selected from DBU, DBN, tertiary amine, N-methylmorpholine, carbonates, potassium, sodium and lithium alkoxides, and sodium, lithium and potassium hydroxides.

4. The process of claim 3 wherein the base is selected from a tertiary amine, DBU or DBN.

5. The process of claim 3 wherein the base is selected from sodium methoxide, sodium ethoxide or potassium tert-butoxide.

6. The process of claim 2 wherein the solvent is DMSO.

7. The process of claim 6 wherein the base is selected from potassium hydroxide, DBU, DBN or N-methylmorpholine.

8. The process of claim 2 wherein the solvent is water.

9. The process of claim 8 wherein the base is carbonates or sodium, lithium and potassium hydroxides.

10. The process of claim 2 wherein the solvent is 2-methoxyethanol.

11. The process of claim 10 wherein the base is selected from potassium, sodium and lithium alkoxides, and sodium, lithium and potassium hydroxides.

12. The process of claim 1 further comprising the step of desalinating the reaction mixture.

13. The process of claim 1 wherein the iohexol is precipitated in the presence of isopropanol.

14. A process for making iohexol comprising the steps of:
   a. heating a first reaction mixture of 5-acetamino-N,N'-bis-(2,3-dihydroxy-propyl)-2,4,6-triiodo-1,3-benzene-dicarboxamide in the presence of DMSO and triethylamine under conditions to achieve dissolution;
   b. adding glycidol to the first reaction mixture to form a second reaction mixture;
   c. maintaining the second reaction mixture for a period of time sufficient to allow the reaction to proceed to completion;
   d. crystallizing iohexol from the second reaction mixture in the presence of isopropanol.

15. The process of claim 14 wherein the second reaction mixture is maintained at about 30°–40° C. for a period of about 72 to about 120 hours.

16. A process for making iohexol comprising the steps of:
   a. Combining 5-acetamino-N,N'-bis-(2,3-dihydroxy-propyl)-2,4,6-triiodo-1,3-benzene-dicarboxamide, a solvent, glycidol, and a tertiary amine to form a reaction mixture;
   b. maintaining the reaction mixture for a period of time sufficient to allow the reaction to proceed to completion; and
   c. isolating iohexol.

* * * * *